United States Patent [19]
Yanagisawa et al.

[11] Patent Number: 5,027,077
[45] Date of Patent: Jun. 25, 1991

[54] HUMIDITY MEASURING APPARATUS

[75] Inventors: Michio Yanagisawa; Masahisa Ikejiri; Hajime Miyazaki; Tsukasa Muranaka; Kunihiro Inoue; Shouichi Uchiyama, all of Suwa, Japan

[73] Assignee: Seiko Epson Corporation, Tokyo, Japan

[21] Appl. No.: 397,619

[22] Filed: Aug. 22, 1989

[30] Foreign Application Priority Data

| Aug. 22, 1988 | [JP] | Japan | 63-207675 |
| Nov. 17, 1988 | [JP] | Japan | 63-290593 |
| Feb. 27, 1989 | [JP] | Japan | 1-45600 |

[51] Int. Cl.$^5$ ............................................. G01R 27/08
[52] U.S. Cl. ................................. 324/712; 73/336.5; 324/694; 324/606
[58] Field of Search ............... 324/691, 693, 694, 711, 324/710, 712, 696, 724, 606; 73/73, 335, 336.5; 340/602

[56] References Cited

U.S. PATENT DOCUMENTS

| 2,988,709 | 6/1961 | Janssen | 324/711 X |
| 3,295,088 | 12/1966 | Smith | 324/696 X |
| 3,490,039 | 1/1970 | Tsao | 324/711 X |
| 3,786,350 | 1/1974 | Munt | 324/712 |
| 4,065,715 | 12/1977 | Jaffe et al. | 324/711 X |
| 4,362,988 | 12/1982 | Weimer | 324/711 X |
| 4,442,422 | 4/1984 | Murata et al. | 324/696 X |
| 4,816,748 | 3/1989 | Tazawa et al. | 324/711 X |

FOREIGN PATENT DOCUMENTS 0125116 11/1984 European Pat. Off. .
015134 7/1981 Japan .
2172999 10/1986 United Kingdom .

Primary Examiner—Kenneth Wieder
Assistant Examiner—Robert W. Mueller
Attorney, Agent, or Firm—Blum Kaplan

[57] ABSTRACT

A humidity sensing apparatus which includes a humidity sensor which detects humidity as a function of impedance is provided. A reference resistor has a predetermined resistance value. A charge switching circuit selectively couples one of the reference resistor or the humidity sensor in series with a reference capacitor which has a predetermined capacitance. A voltage judging circuit determines whether the terminal voltage of the reference capacitor is high or low. A charge/discharge switch selectively charges and discharges the reference capacitor in accordance with the output of the voltage judging circuit. A sensor direction switching circuit inverts the direction of current flowing through the humidity sensor during charging of the reference capacitor. An oscillation frequency counter counts the number of charge/discharge cycles which are repeated during a predetermined time period. A humidity sensor resistance value calculating circuit calculates the resistance value of the humidity sensor in accordance with the number of repeated charge/discharge cycles when the reference capacitor is coupled to the reference resistor for charging and the number of repeated charge/discharge cycles when the reference capacitor is coupled to the humidity sensor during charging. A humidity determining circuit determines the humidity from the resistance value of the humidity sensor calculated by the humidity sensor resistance value calculating circuit.

20 Claims, 11 Drawing Sheets

HUMIDITY MEASURING APPARATUS

BACKGROUND OF THE INVENTION

This invention relates to a humidity sensing apparatus and more particularly to a humidity sensor which detects humidity by measuring the change in the electrical characteristic of an element corresponding to the ambient humidity.

The need for humidity measurement and humidity control has recently been increasing and the importance of a humidity sensor is widely recognized. There are several types of humidity sensors which detect humidity by measuring the change in the electrical characteristics of an element corresponding to the ambient humidity, including electrolytic, metallic, polymeric and ceramic humidity sensors. These humidity sensors have been extensively studied and polymeric and ceramic humidity sensors have been put to practical use. Each of the sensors measures the humidity level by measuring the change in the resistance of an element or the change in the electrostatic capacity of an element as the element absorbs or releases moisture. A resistance-change type humidity sensor detects humidity by measuring the change in the resistance of an element in accordance with the ambient humidity. A capacitance-change type humidity sensor detects humidity by measuring the change in the electrostatic capacity of an element in accordance with the ambient humidity.

An electronic thermometer which measures temperature using a resistance-change type temperature sensor is known from Japanese Patent Laid-Open No. 15134/1983. The structure of the electronic thermometer may also be used to measure humidity. However, electrolysis results and moisture sensitivity changes if current flows through the humidity sensor in only one direction for a long time period. Thus, accurate humidity measurement is not possible.

Many of the conventional resistance-change type humidity sensors have such high resistance at low humidity that it is difficult to measure low humidity with high accuracy. In order to construct a humidity sensor which is able to measure low humidity with high accuracy, high quality circuitry and a highly accurate mounting technique are required, leading to an increase in manufacturing costs.

Generally, in a resistance-change type humidity sensor, the logarithm of resistance changes linearly with respect to the change in relative humidity. If the linearity is good, a logarithm amplifier is capable of compensating the linearity. In conventional humidity sensors, however, the linearity is poor. Thus, a complicated linearity compensation circuit is required to produce a highly accurate hygrometer.

Additionally, in a resistance-change type humidity sensor, the greater the rate of change in the resistance between low humidity and high humidity, the greater the sensitivity. However, when a hygrometer is produced, it is difficult to provide the dynamic range for the measuring circuit if the rate of change in the resistance between low humidity and high humidity is too large.

In a capacitance-change type humidity sensor, the linearity of change in electrostatic capacity with respect to relative humidity is poor. Thus, a complicated linearity compensation circuit is required to produce a highly accurate hygrometer. In addition, many capacitance-change type humidity sensors have poor stability at high humidity. Consequently it is difficult to measure high humidity with high accuracy.

In conventional humidity sensors moisture sensitivity is highly dependent on the temperature and a temperature compensation circuit is required. When temperature dependence is represented by a simple function, it is not necessary to have a complicated temperature compensation circuit. However, in conventional humidity sensors dependence of moisture sensitivity on temperature is not represented by a simple function and a complicated temperature compensation circuit is required to produce a highly accurate hygrometer. Although a complicated temperature compensation circuit may be provided, complete temperature compensation is difficult in a place in which the change of temperature is large. This is due to a difference in thermal response between the humidity sensor and the temperature sensor, or difference in the location of the temperature sensor and the humidity sensor. In other words, as long as moisture sensitivity of the humidity sensor is dependent on temperature, accurate humidity measurement remains difficult.

As the prior art illustrates a highly accurate hygrometer is difficult to produce. A conventional humidity sensor is expensive to manufacture since it requires high quality circuitry and a highly accurate mounting technique. Additionally, inspection and control of the humidity sensor require a large amount of time.

Accordingly, it is desirable to provide an improved humidity sensor which eliminates these problems associated with prior art devices and accurately measures humidity.

SUMMARY OF THE INVENTION

Generally speaking, in accordance with the invention, an improved humidity measuring apparatus which measures the humidity level by measuring the change in the resistance of an element is provided. A humidity sensor has an impedance which varies in accordance with changes in the humidity level. The humidity sensor is coupled to a reference resistor having a predetermined resistance value. A charge switching circuit which connects either reference resistor to a reference capacitor to charge the capacitor. A sensor direction switching circuit couples the charge switching circuit to the humidity sensor and inverts the direction in which current flows through the humidity sensor during charging.

A voltage judging circuit determines whether the terminal voltage of the reference capacitor is high or low. A charge/discharge switching circuit is coupled to the charge switching circuit and selectively switches between charging and discharging the reference capacitor in accordance with the output of the voltage judging circuit. A discharge resistor is coupled to the reference capacitor through the charge/discharge switching circuit. By switching from charging the reference capacitor to discharging the reference capacitor, a charge/discharge cycle is generated. An oscillation frequency counter counts the number of cycles of charge and discharge which are repeated within a predetermined time period. A humidity sensor resistance value calculating circuit calculates the resistance value of the humidity sensor based upon the number of repeated charge/discharge cycles by comparing the number of cycles generated when the reference capacitor is coupled to the reference resistor and the number of repeated cycles when the reference capacitor is coupled to the humidity sensor during charging. A humidity determining circuit determines the humidity based upon the resistance value calculated by the humidity sensor resistance value calculating circuit.

The humidity sensor includes a pair of electrodes spaced apart on an insulating substrate, a porous silica film with carbon particles dispersed throughout formed across the substrate and electrodes, and a silica film disposed on the surface of the porous silica film.

Accordingly, it is an object of this invention to provide an improved humidity sensor capable of measuring humidity in a highly accurate manner.

Another object of the invention is to provide an improved humidity sensor having constant moisture sensitivity in which electrolysis does not occur.

A further object of the invention is to provide an improved humidity sensor in which the electrical characteristics do not vary and which does not require constant adjustment.

Still other objects and advantages of the invention will in part be obvious and will in part be apparent from the specification.

The invention accordingly comprises the several steps and the relation of one or more of such steps with respect to each of the others, and the article possessing the features, properties, and the relation of the elements, which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
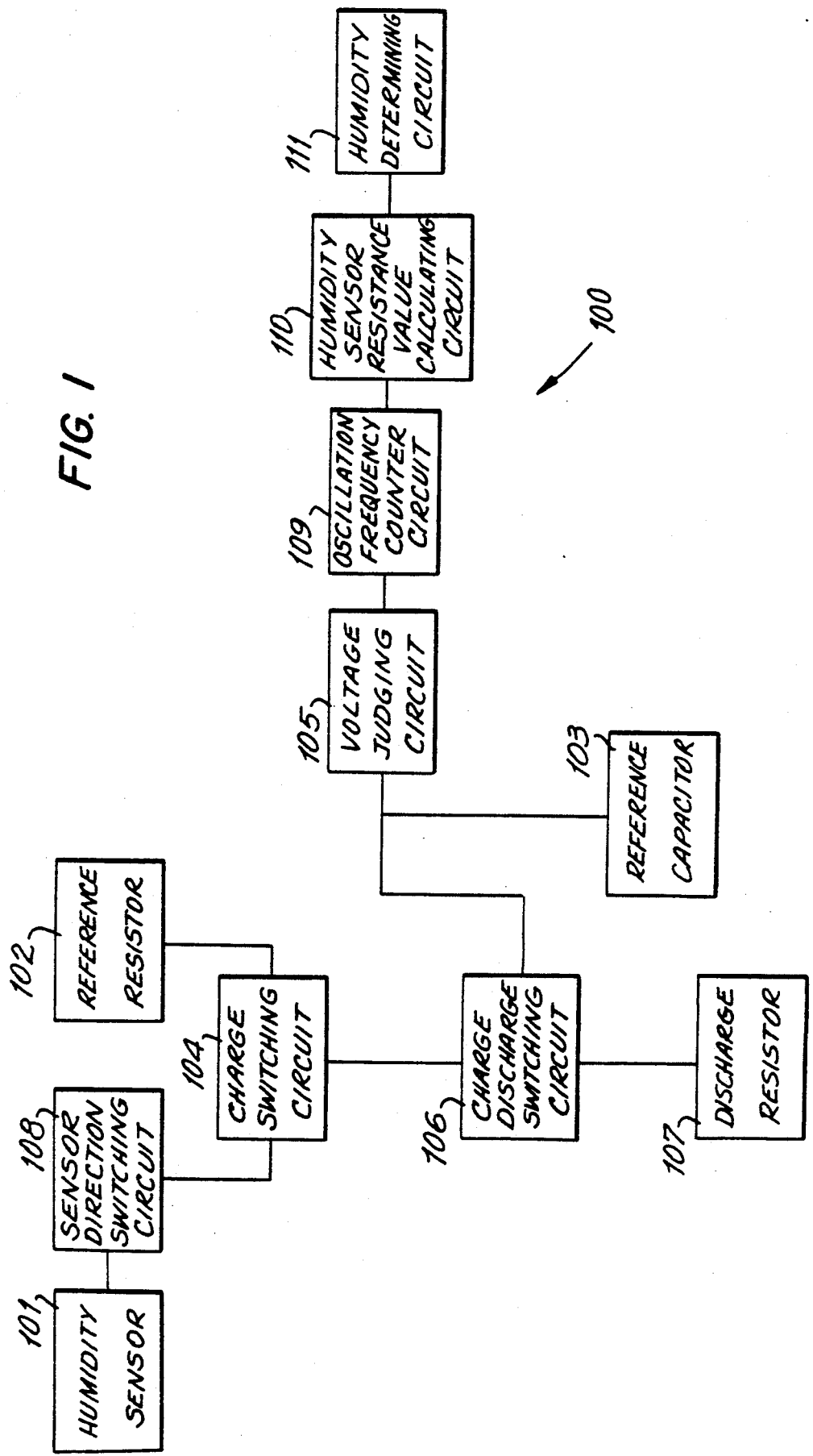
FIG. 1 is a block diagram of a humidity measuring apparatus constructed in accordance with the invention.

Reference is made to FIG. 1 in which an apparatus for measuring the humidity, generally indicated at 100, constructed in accordance with the invention is provided. Humidity measuring apparatus 100 includes a humidity sensor 101 having an impedance which varies in accordance with the changes in humidity. A reference resistor 102 has a predetermined resistance value. Reference resistor 102 is coupled to humidity sensor 101 by a charge switching circuit 104 which connects either reference resistor 102 or humidity sensor 101 to a reference capacitor 103 to charge reference capacitor 103 from a DC power source. A sensor direction switching circuit 108 couples charge switching circuit 104 to humidity sensor 101 and inverts the direction of current flowing within humidity sensor 101 during the charging of reference capacitor 103 by switching the direction in which humidity sensor 101 is connected to charge switching circuit 104.

A voltage judging circuit 105 determines whether the terminal voltage of the reference capacitor 103 is high (H) or low (L). A charge/discharge switching circuit 106 coupling reference capacitor 103 to charge switching circuit 104 selectively switches between charging and discharging reference capacitor 103 in accordance with the output of voltage judging circuit 105. A discharge resistor 107 coupled to reference capacitor 103 by charge/discharge switching circuit 106 acts as a load resistor for reference capacitor 103 during the discharge of reference capacitor 103. By switching from charging reference capacitor 103 to discharging reference capacitor 103 a charge/discharge cycle is generated.

An oscillation frequency counter circuit 109 counts the number of charge/discharge cycles generated by reference capacitor 103 which are repeated within a predetermined time period. A humidity sensor resistance value calculating circuit 110 calculates the resistance value of humidity sensor 101 based upon the number of repeated charge/discharge cycles when reference capacitor 103 is coupled to reference resistor 102 and the number of charge/discharge repeated cycles when reference capacitor 103 is coupled to humidity sensor 101 during charging. A humidity determining circuit 111 determines the humidity based upon resistance value calculated by humidity sensor resistance value calculating circuit 110.

Figure 2:
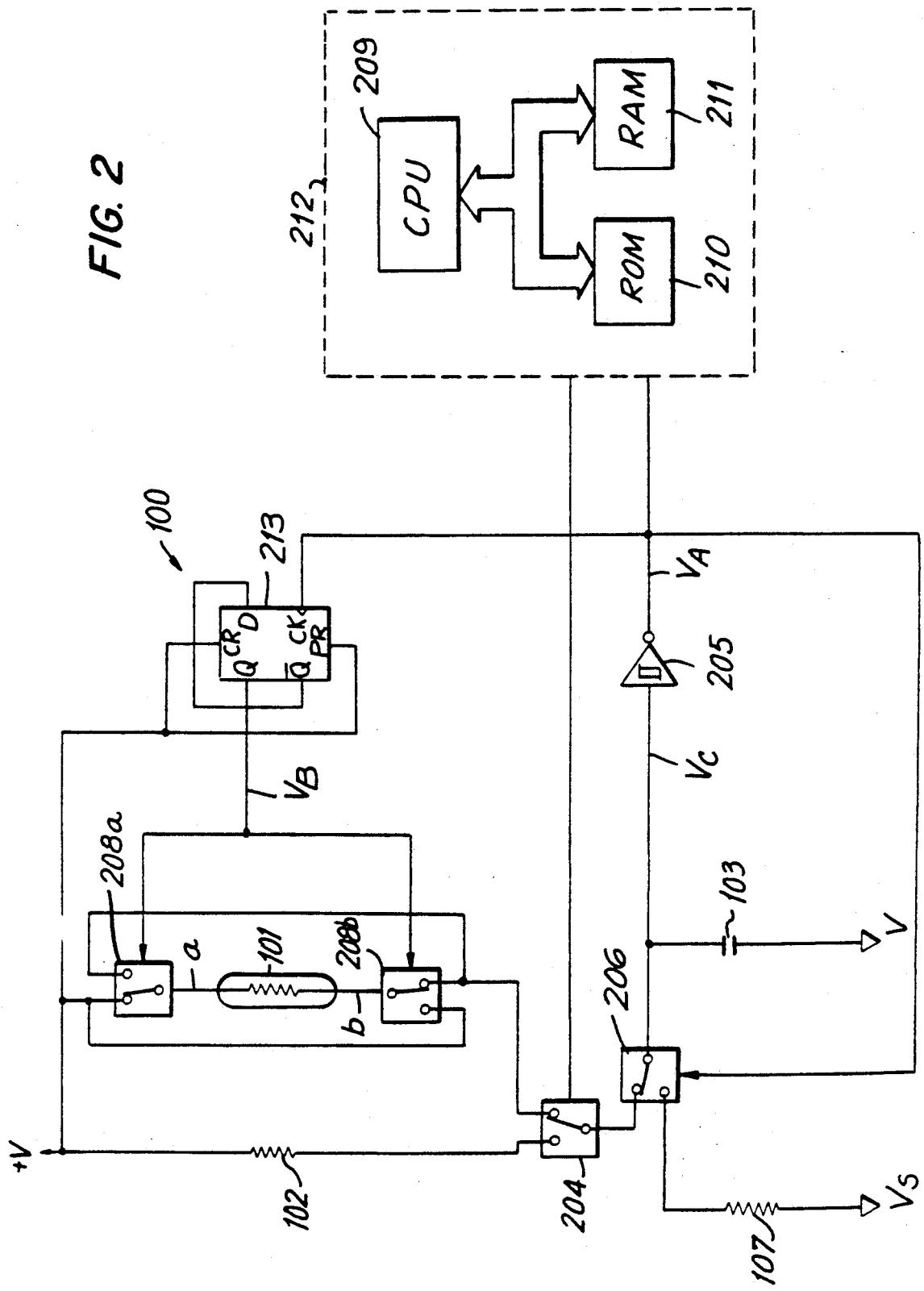
FIG. 2 is a circuit diagram of a humidity measuring apparatus constructed in accordance with the invention.

Reference is now made to FIG. 2, a circuit diagram of one embodiment of the humidity measuring apparatus 100 of FIG. 1. Humidity sensor 101 is positioned between the common terminals of a first switch 208a and a second switch 208b which act in concert to switch the direction of the current flow path within sensor 101, thus acting as sensor direction switching circuit 108. Switches 208a, 208b are analog switches which are coupled to each other as well as to a flip flop 213. Flip flop 213 produces a Q output having a voltage $V_B$ input at 208a, 208b. The D output of flip flop 213 is fed back as the $\overline{Q}$ input of flip flop 213.

A reference resistor 102 is serially placed between a voltage drain and one switch terminal of an analog switch 204. A second switch terminal of switch 204 is coupled to a second switch terminal of switch 208b, so that switch 204 acts as a charge switching circuit. A first switch terminal of switch 208a is coupled to the voltage source and to a first switch terminal of switch 208b, a second switch terminal of switch 208a is coupled to the second switch terminal of switch 208b.

An analog switch 206 has a first switch terminal coupled to the common terminal switch 204 and a second switch terminal coupled to discharge resistor 107. Switch 206 is an analog switch which is controlled by the output of inverting gate 205. Reference capacitor 103 is coupled to the common terminal of switch 206 at one end and to the voltage source at the other end, so that switch 206 acts as a charge/discharge switching circuit. A logic inverting gate 205 is coupled to capacitor 103 and receives an input $V_c$ and outputs a voltage $V_A$ in response to the charging and discharging of reference capacitor 103.

Figure 4:
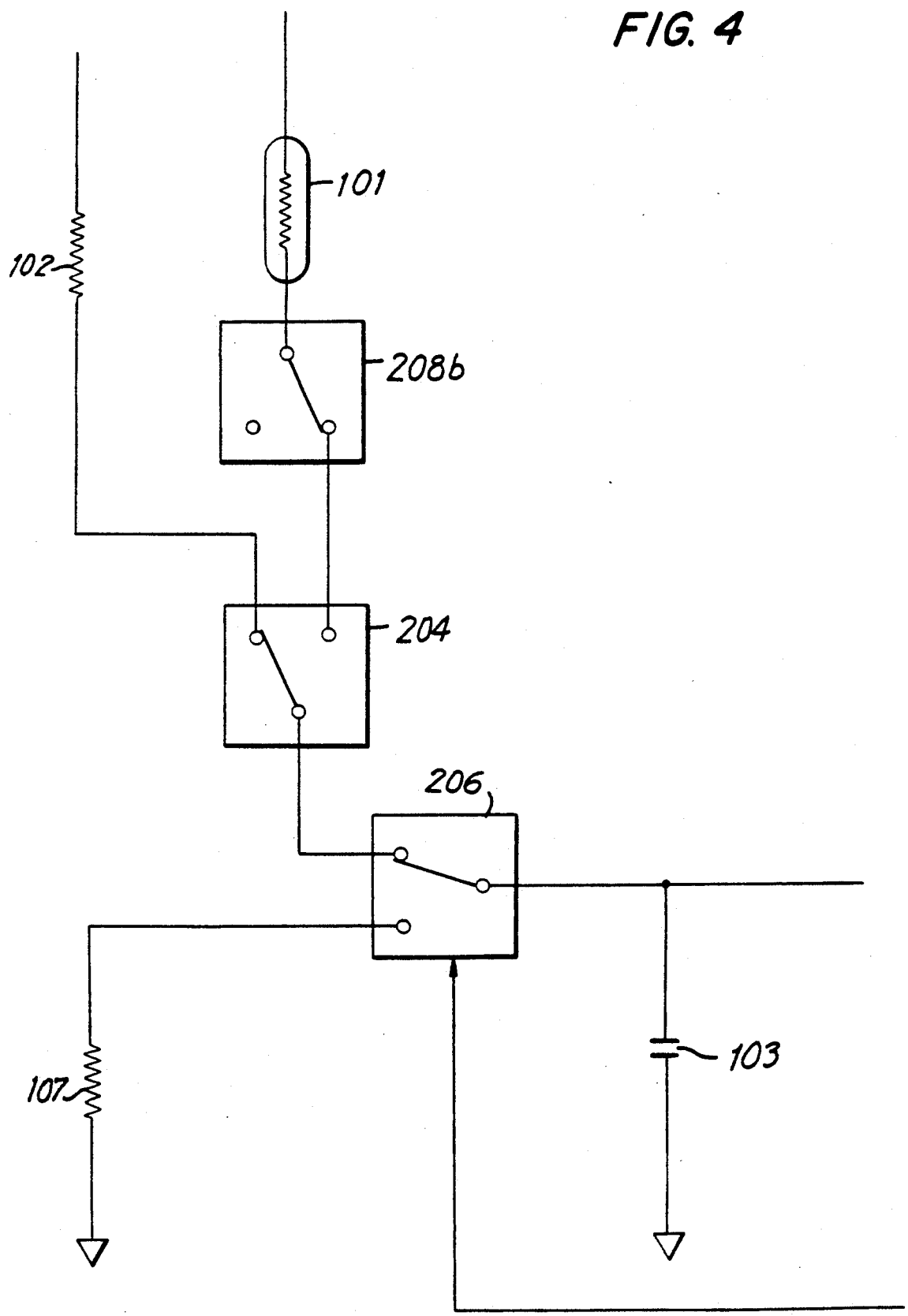
FIG. 4 is a partial circuit drawing of the humidity measuring apparatus showing the charging of the capacitor utilizing the reference resistor.

To measure humidity, reference resistor 102 is first selected by analog switch 204 which is provided as a charge switching circuit to form a current pathway between reference capacitor 103 and reference resistor 102 as shown in FIG. 4. When analog switch 206 is positioned as shown in FIG. 4 reference capacitor 103 is being charged. The terminal voltage $V_c$ of reference capacitor 103 then increases with time.

Figure 7:
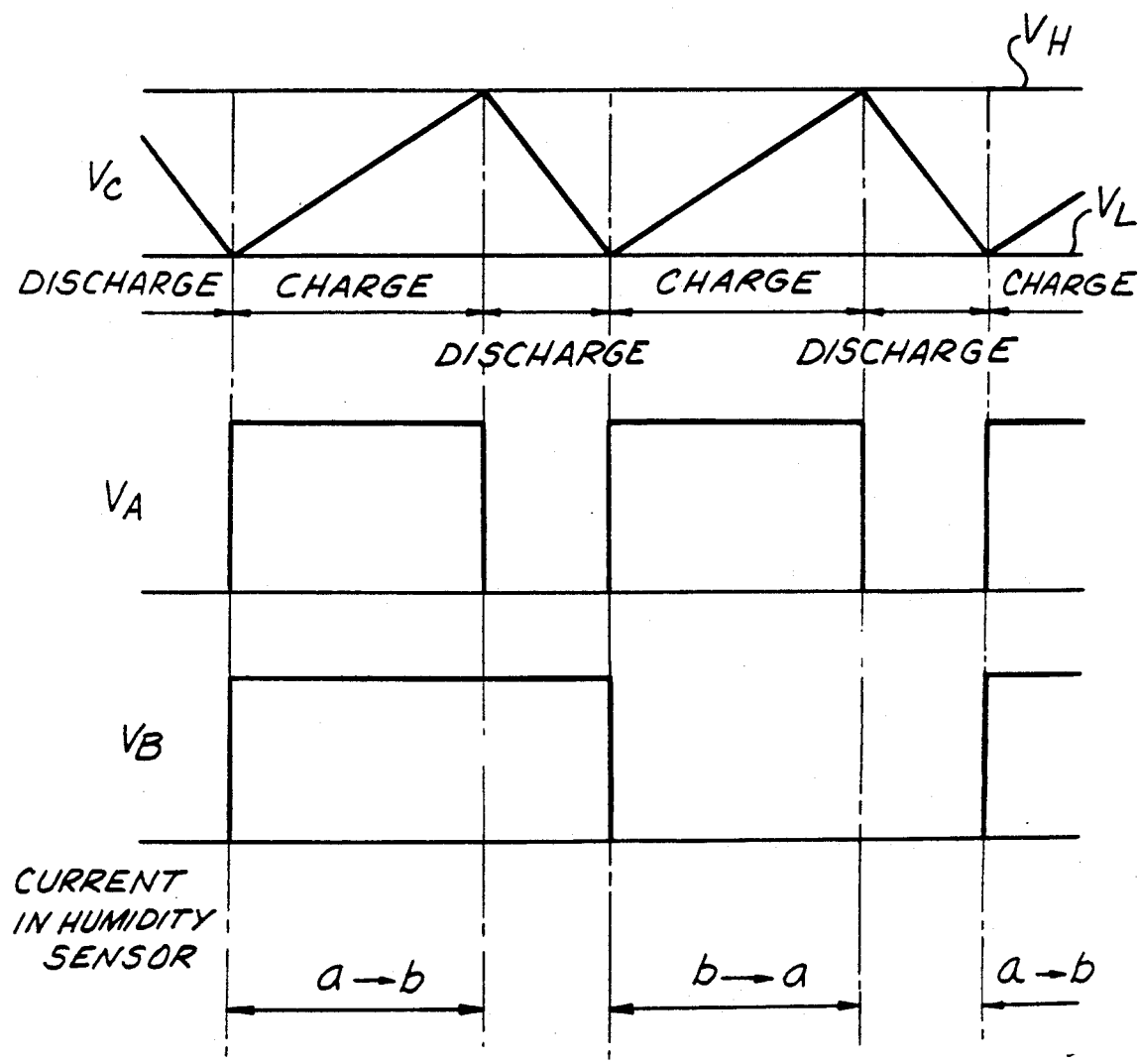
FIG. 7 is a graphical representation of the voltage output during operation of the sensor direction switching circuit.

Logic inverting gate 205 having hysteresis properties acts as a voltage judging circuit. When the terminal voltage $V_c$ output by capacitor 103 reaches an upper threshold voltage $V_H$ of logic inverting gate 205, as shown in FIG. 7 the output $V_A$ of logic inverting gate 205 becomes low (L). $V_A$ is fed back to analog switch 206, causing analog switch 206 to switch to a discharging mode.

Figure 5:
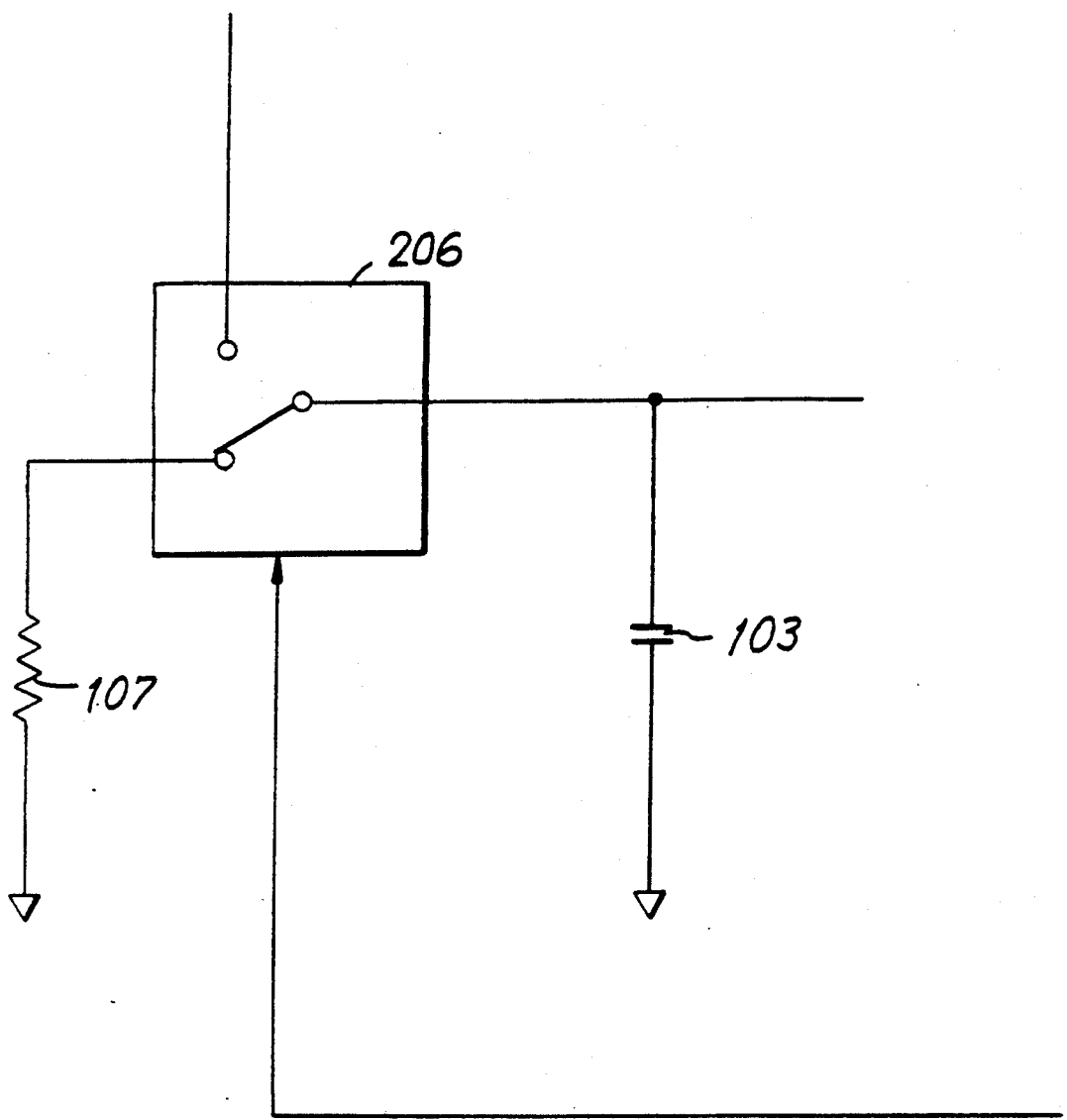
FIG. 5 is a partial circuit drawing showing the discharging of the capacitor.

During discharging, reference capacitor 103 is connected to discharge resistor 107 as shown in FIG. 5 causing the terminal voltage $V_C$ to decrease with time. When terminal voltage $V_C$ decreases to the low threshold voltage $V_L$ of logic inverting gate 205, as shown in FIG. 7, the output $V_A$ reaches an H level causing switch 206 to change to a charging mode. In this way, a repeating charge/discharge cycle occurs.

Oscillation frequency counter circuit 109 (FIG. 1) counts the number of charge/discharge cycles produced by reference capacitor 103 which are repeated within a predetermined time period T. An exemplary embodiment oscillation frequency counter circuit 109 is a microcomputer 212 which includes a CPU 209, a ROM 210 and a RAM 211 to count the number of cycles. The number of cycles counted when analog switch 206 couples capacitor 103 to reference resistor 102 is N.

Figure 6:
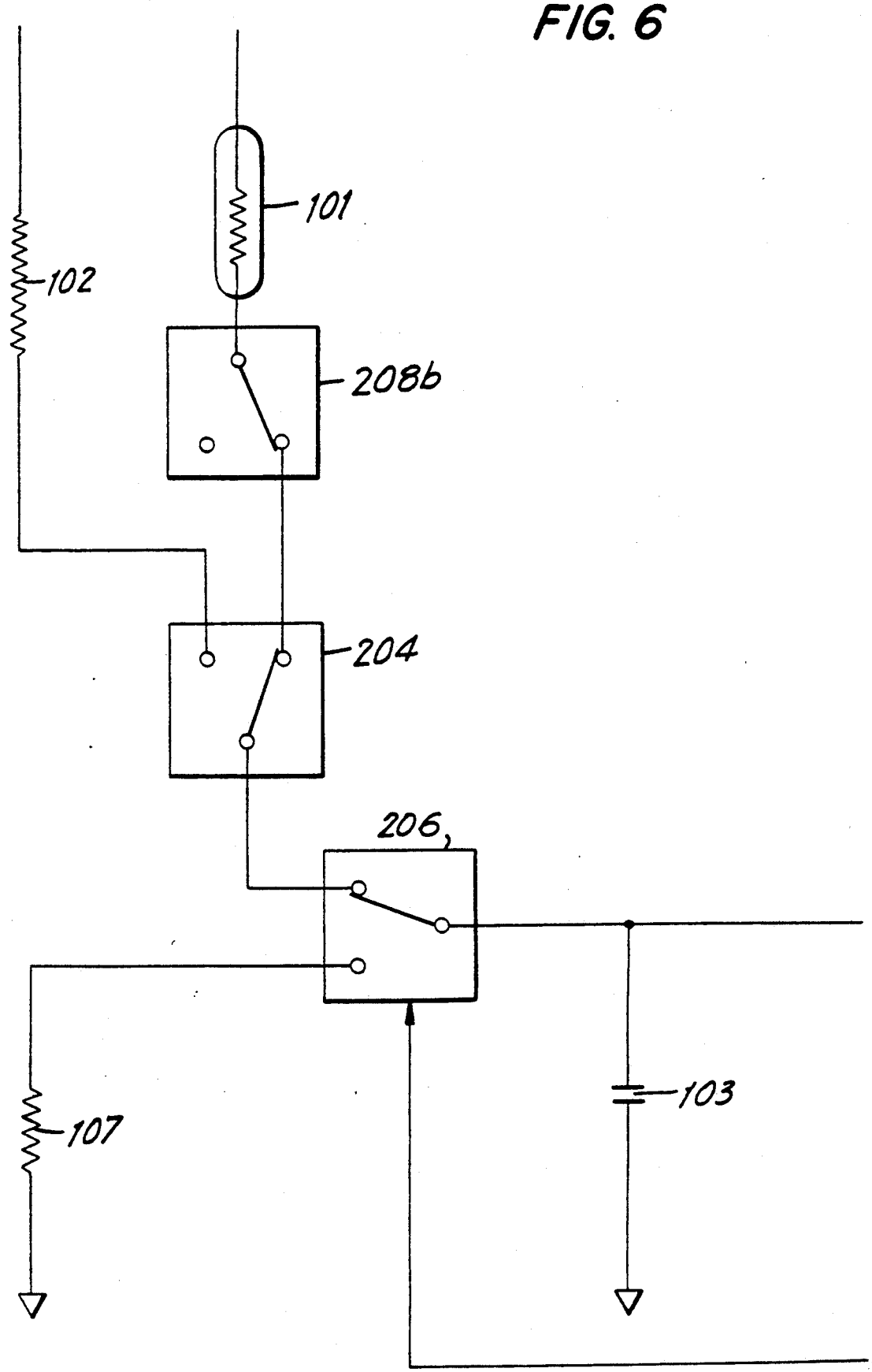
FIG. 6 is a partial circuit diagram showing the charging of the capacitor utilizing the humidity sensor.

Switch 204 is switched to connect humidity sensor 101 to reference capacitor 103 as shown in FIG. 6. A charge/discharge cycle for reference capacitor 103 repeats in the same way as when reference resistor 102 is selected by switch 204 and the number of repeated cycles is counted by microcomputer 212. The number of cycles counted when humidity sensor 101 is coupled to capacitor 103 is $N_s$.

Analog switch 208 consisting of switches 208a and 208b changes the direction in which humidity sensor 101 is connected within the humidity measuring apparatus 100 during charging so that the direction of current flow is changed. More specifically analog switches 208a and 208b are controlled by a frequency divider which utilizes flip flop 213. If humidity sensor 101 is considered as having a first terminal a and a second terminal b, the current flow direction between terminals a and b switches at every charge/discharge cycle. The switching function is necessary to avoid electrolysis or the like within humidity sensor 101 and therefore overcomes the problems in the prior art humidity sensors.

The resistance value $R_S$ of humidity sensor 101 may be calculated from the following formula based upon the values N, $N_S$. The resistance value $R_n$ of the reference resistor 102 is known. The resistance value $R_s$ may be defined in terms of the resistance of reference resistor 102 $R_n$, as follows:

$$R_s = (N/N_S) R_n \quad (1)$$

Deriving from this first formula it is assumed that the charging time period when using reference resistor 102 is $T_{nc}$, the charging time utilizing humidity sensor 101 is $T_{sc}$, the discharging time is $T_d$, the resistance value of the discharge resistor 107 is Rd and the capacitance of the reference capacitor 103 is C. Applying the rules for capacitor resistance circuits, the charge time and discharge time may be expressed as follows:

$$T_{nc} = CR_n \cdot \ln[(V-V_L)/(V-V_H)]$$

$$T_{sc} = CR_s \cdot \ln[(V-V_L)/(V-V_H)]$$

$$\text{i } T_d = CR_d \cdot \ln(V_H/V_L)$$

In accordance with the definition of N and $N_s$, the time period T may be expressed as follows:

$$T = N(T_{nc} = T_d) = N_s(T_{sc} + T_d)$$

If the resistance value of $R_d$ of the discharge resistor 107 is set at a sufficiently small value when compared with $R_n$ and $R_s$, $$T_{nc} >> T_d, T_{sc} >> T_d$$

Therefore, the following formula holds:

$$NT_{nc} = N_s T_{sc}$$

Namely, $$NR_n = N_s R_s$$

which results in formula 1.

Humidity sensor resistance value calculating circuit 110 executes the calculation of formula 1 utilizing microcomputer 212.

N is obtained by using reference resistor 102 because the capacitance of the capacitor is more likely to change in accordance with the change in temperature, whereas use of reference resistor 102 provides accurate humidity measurement even if the temperature changes.

The capacitance of reference capacitor 103 need not be strictly measured, but may be used as a reference for determining measuring time T.

Figure 8:
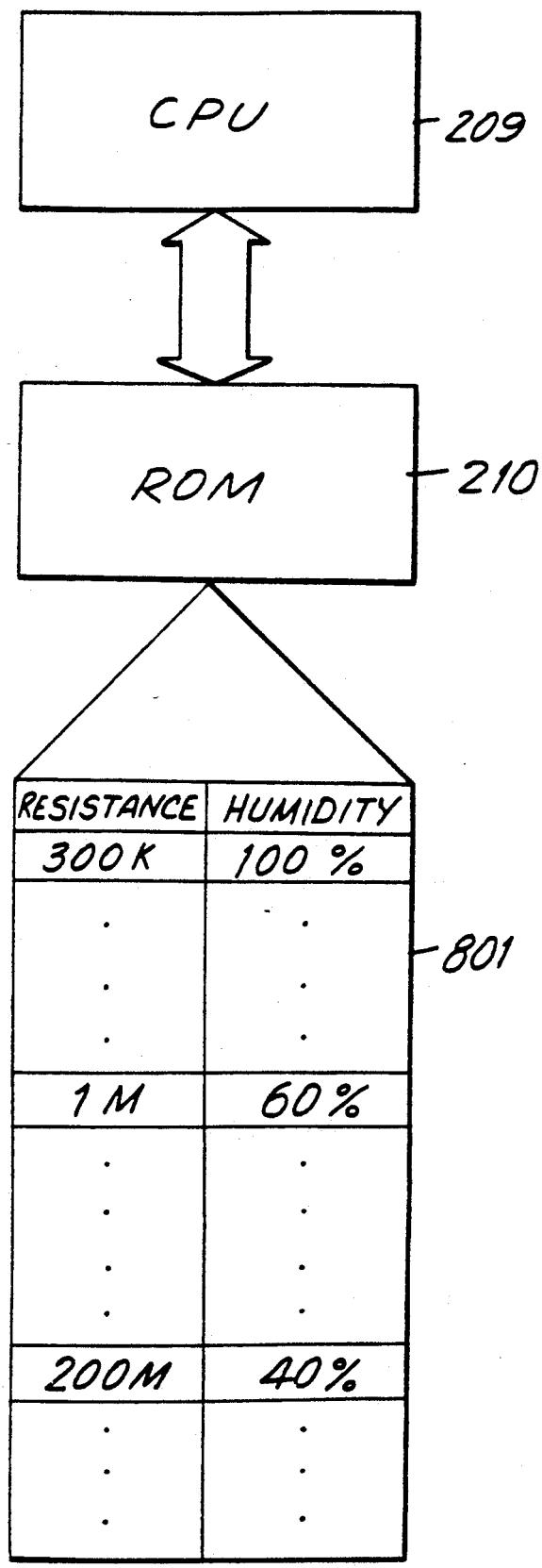
FIG. 8 is a block diagram of an oscillation frequency counter constructed in accordance with the invention.
Figure 11:
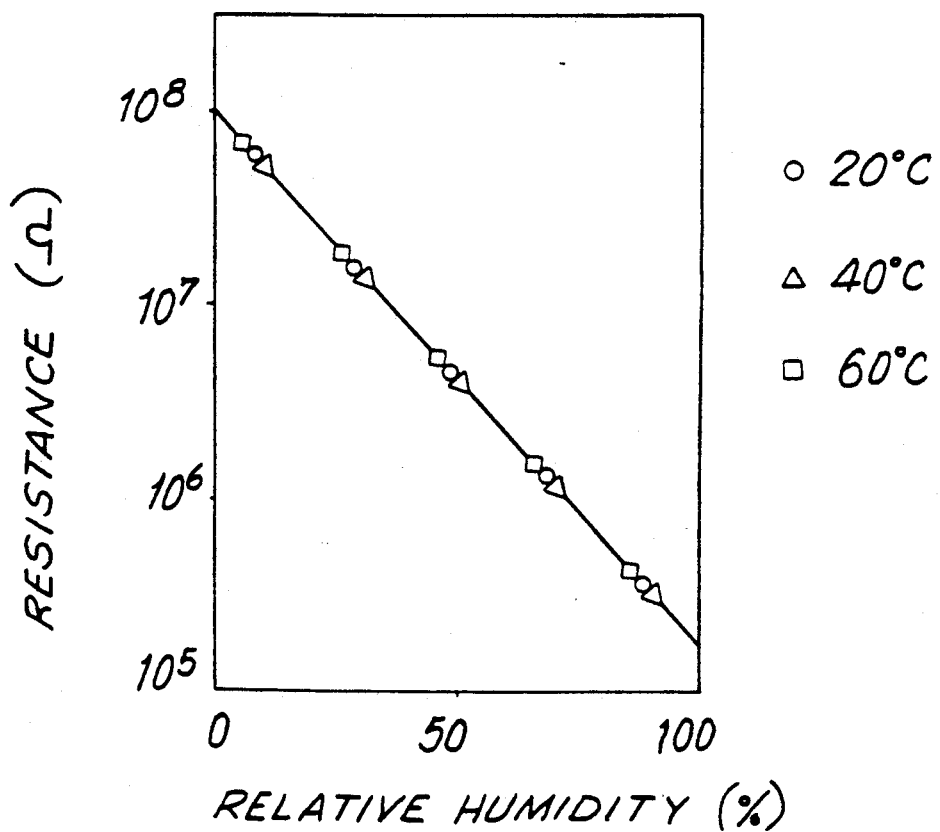
FIG. 11 is a graph showing the relationship between relative humidity and resistance for the humidity sensor of FIG. 10.

Humidity determining circuit 111 determines the humidity from the resistance value of humidity sensor 101. As seen in FIG. 8, a table 801 mapping resistance values and humidity is stored in ROM 210. ROM 210 is read by CPU 209 in a conventional known manner. By utilizing a humidity sensor 101 having resistance humidity characteristics as shown in FIG. 11, it is possible to determine the humidity by executing a simple calculation by microcomputer 212. The formula for calculating the humidity of Rh (%) from the resistance value Rs of humidity sensor 101 is as follows:

$$Rh = P \cdot \log Rs + Q \qquad (2)$$

wherein P and Q are constants determined by the characteristics of humidity sensor 101.

Figure 3:
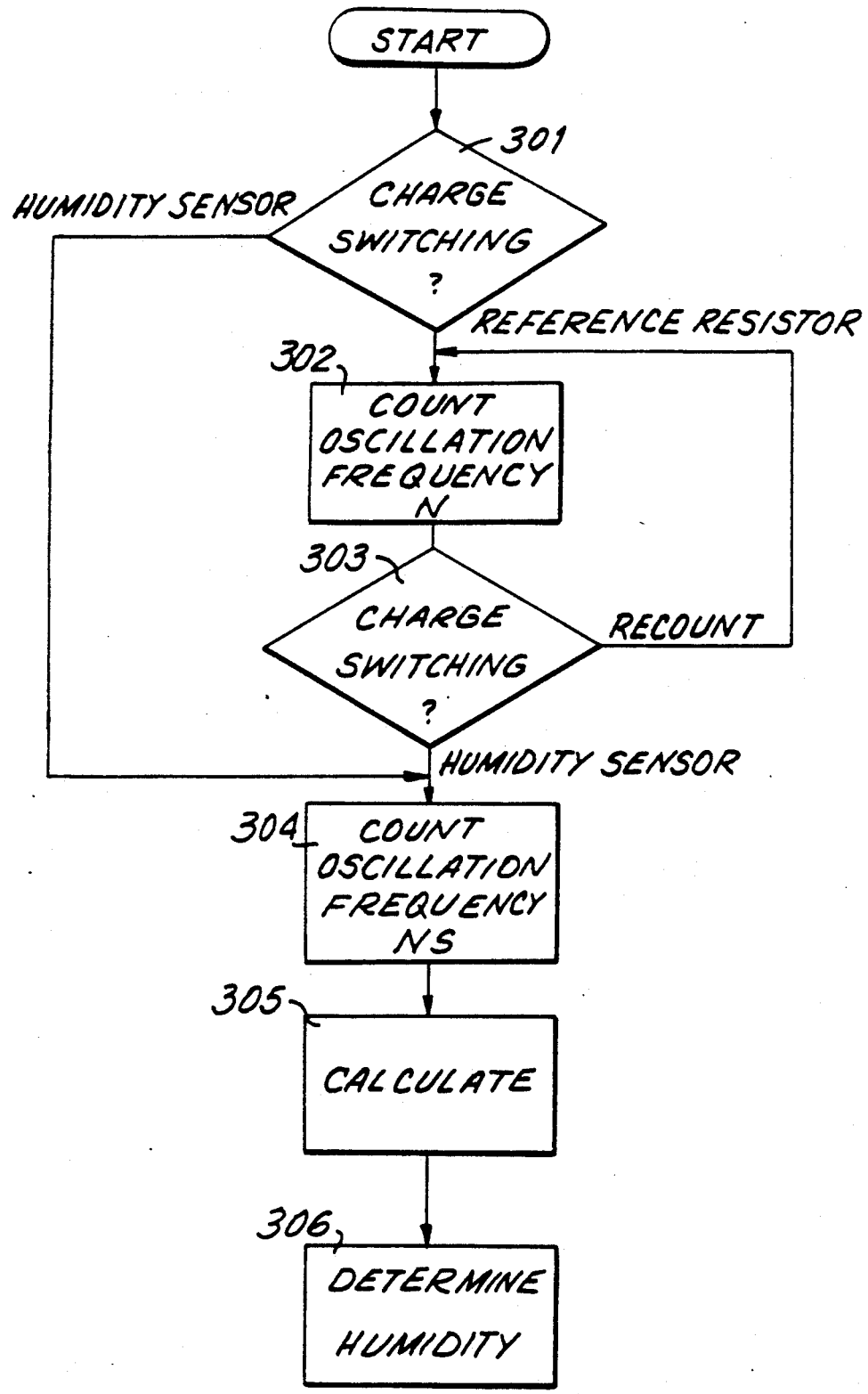
FIG. 3 is a flow chart for the operation of the humidity measuring apparatus constructed in accordance with the invention.

Reference is made to FIG. 3 in which a flow chart for measuring humidity utilizing humidity sensor 101 within humidity measuring apparatus 100 is provided. A measurement is carried out at predetermined time intervals or in accordance with an external command.

In a step 301, it is determined whether charge switching circuit 104 is causing measurement to be conducted by charging with humidity sensor 101 or charging with reference resistor 102. If it is determined that reference resistor 102 is selected oscillation frequency is counted in accordance With a step 302. Measurement utilizing reference resistor 102 is done only in the beginning of operation of the apparatus if the temperature change in the measured atmosphere is small.

Figure 9:
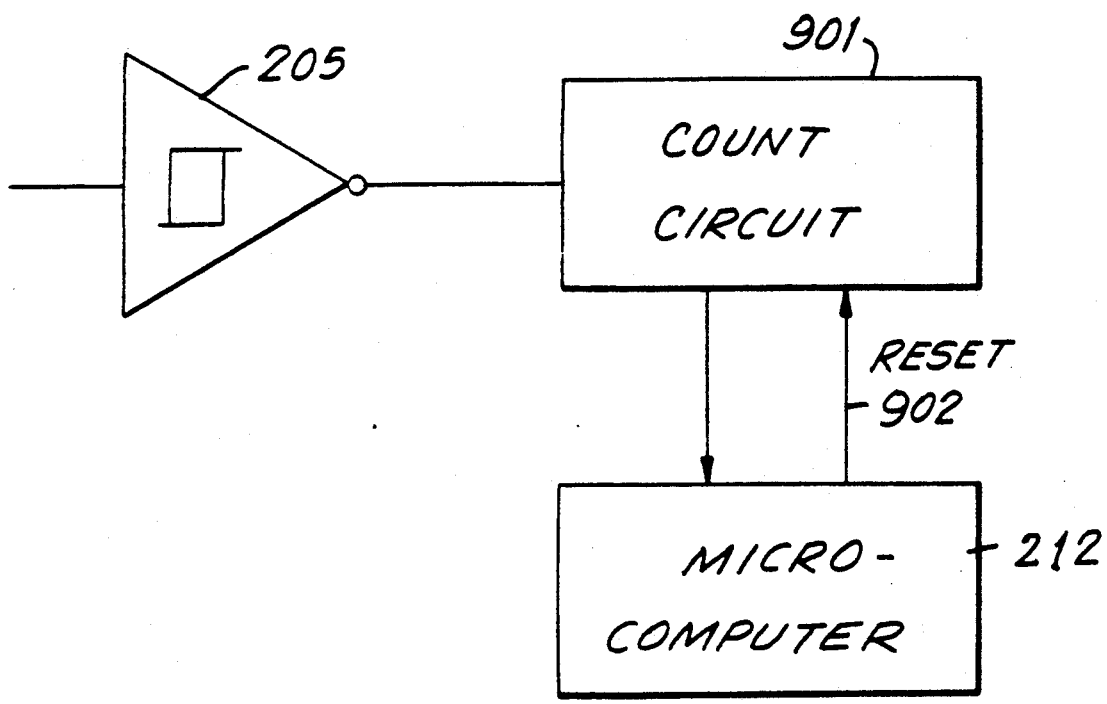
FIG. 9 is a block diagram oscillation frequency counter constructed in accordance with a second embodiment of the invention.

It is possible to repeat the count in step 302 several times in order to increase measuring accuracy in a step 303. The number of cycles counted in 302 becomes N. If the number is not recounted in step 303 or humidity sensor 101 is selected in step 301, then the oscillation frequency of the charge/discharge cycle is repeated within a predetermined time T is counted in a step 304 by microcomputer 212. The oscillation frequency counter may utilize a counter circuit 901 which is resettable by microcomputer 212 as shown in FIG. 9. This is a convenient structure when microcomputer 212 is used for multiple tasks. In a step 305, the resistance value of humidity sensor 101 is determined. More specifically, formula 1 is calculated. After the resistance of humidity sensor 101 is calculated the humidity is determined in a step 306. Counting the oscillation pulses, calculating formulas 1 and 2 and reading the ROM data are carried out by methods known in the art.

Figure 10:
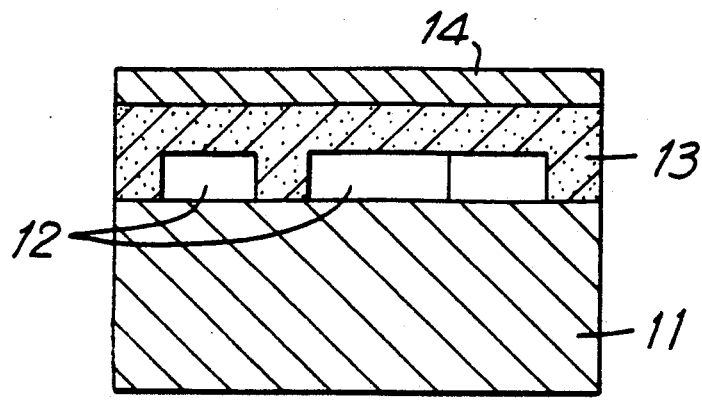
FIG. 10 is a sectional view of a humidity sensor constructed and arranged in accordance with the invention.

A humidity sensor 20 (described in detail in applicants' co-pending U.S. patent application Ser. No. 07/370,725 and incorporated as is fully set forth herein) constructed in accordance with the invention is shown in cross-section in FIG. 10. Humidity sensor 20 includes an insulating substrate 11 and a pair of electrodes 12 provided on insulating substrate 11. A porous silica film 13 containing carbon particles is disposed over insulating substrate 11 and electrodes 12. A silica film 14 is disposed over porous silica film 13.

Insulating substrate is formed of an insulating material. Preferably, it is an alumina substrate in terms of reliability and the ability to mass produce the humidity sensor.

Figure 12:
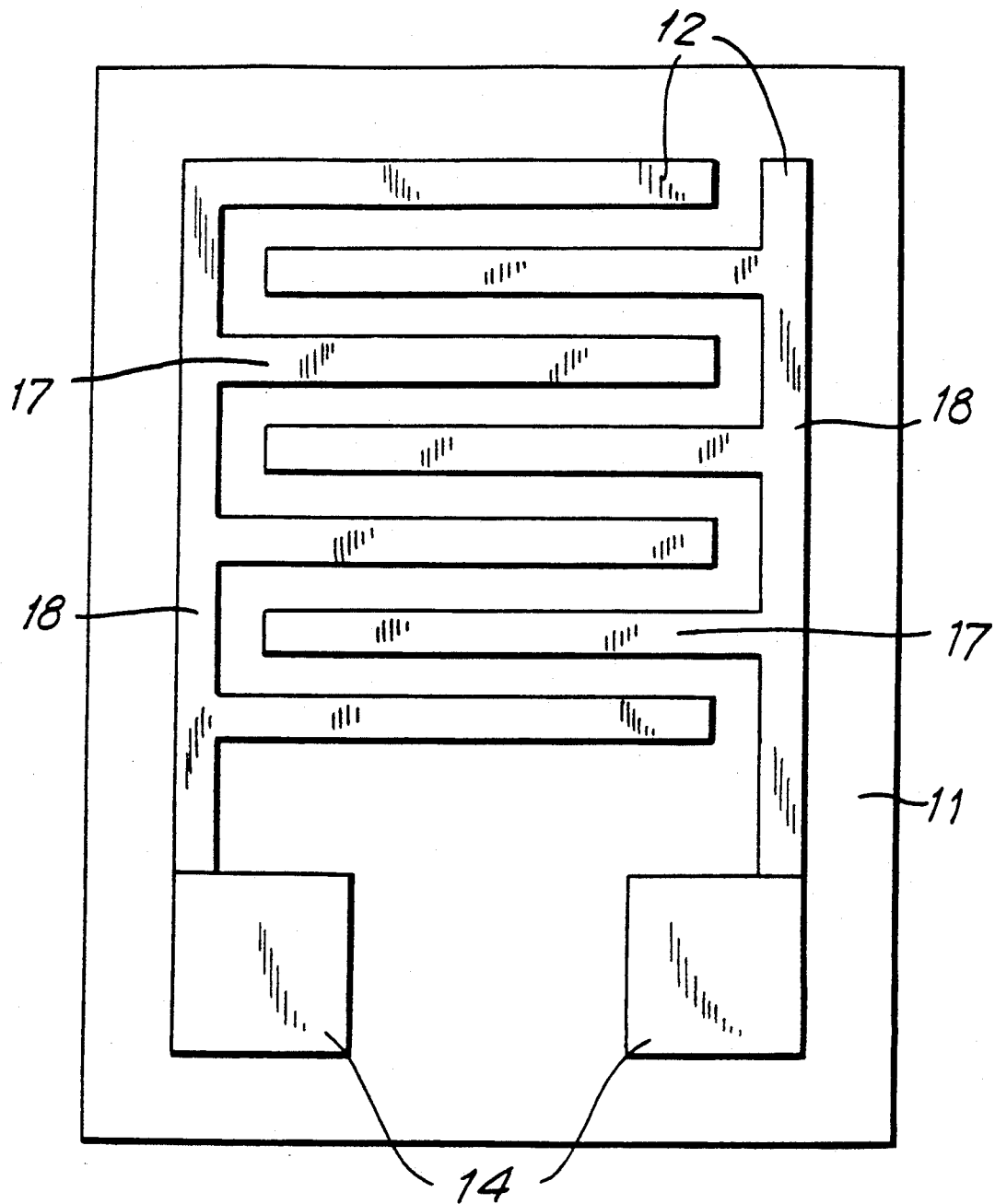
FIG. 12 is a top plan view of the humidity sensor constructed in accordance with the invention.

As seen in FIG. 12 electrodes 12 are formed in the shape of comb electrodes, each of which have a base member 18 and teeth 17 like that of a comb ending at terminal portions 14, in order to reduce the resistance of humidity sensor 20. Teeth 17 are interlaced in alternating fashion. Electrodes 12 are formed of Cr at the portion at which porous silica film 13 is deposited. At the portions to which lead wires are connected, electrode 12 is formed in multi-layered structure. This multi-structure is formed by depositing a Cr electrode layer on insulating substrate 11, depositing an Au electrode layer on the Cr electrode layer, depositing a NiCr electrode layer on the Au electrode layer and depositing an Au electrode layer on the NiCr electrode layer.

By varying the content of the carbon particles dispersed on the porous silica film, conductivity freely varies. Thus the linearity of the change in resistance with respect to the change in relative humidity is improved. It is possible to measure a wide range of humidity levels with high accuracy by this device. It is easy to measure low humidity, which increases the resistance of the humidity sensor.

The relationship between relative humidity and the logarithm of the resistance is linear in a conventional resistance-change type humidity sensor. In a humidity sensor constructed in accordance with the invention, it is also possible to maintain the linear relationship between the relative humidity and the resistance by controlling the carbon particle content. This permits dispensing with the need for a logarithm amplifier. The resistance of a humidity sensor constructed in accordance with the invention is also reduced by reducing the gap between the electrodes since the electrodes are formed by sputtering.

In addition, since dependence of moisture sensitivity on temperature is low, a temperature compensation circuit is not necessary. The characteristics of the humidity sensor do not deteriorate even in severe environments since the carbon particle and the silica film are chemically stable. Thus, a humidity sensor prepared in accordance with the invention is highly accurate and highly reliable.

The content of carbon particles in the silica sol is between about 1 and 4 wt %, and preferably 2.5 wt %. If the content of carbon particles exceeds about 4 wt %, the the silica sol becomes unstable.

The porous silica film containing carbon particles is easily formed. First, a silica sol with carbon particles dispersed throughout is formed by dispersing silica particles and carbon particles in a hydrolyzed solution of alkoxide. The silica particles and the carbon particles may be dispersed either before or after hydrolysis of the silicon alkoxide. The sol is formed into a film and the resulting film is heat treated to form the porous silica film containing carbon particles, thus the carbon particle content is easily controlled by the amount of carbon particles dispersed in the silica sol. When the above described sol is formed into a film, a dip coating method is performed.

The silica film formed on the porous silica film containing carbon particles functions as a protective film for the porous silica film having carbon particles thus enhancing the mechanical strength of the porous silica film containing carbon particles and improving the durability and reliability of the humidity sensor.

As described above, since it is easy to manufacture a humidity sensor in accordance with the invention, the humidity sensor is easily mass produced. The manufacturing cost is also low due to the low cost of the raw materials and it is possible to produce an inexpensive humidity sensor. Thus, in accordance with the invention it is possible to mass produce a highly accurate and reliable humidity sensor.

The invention will be better understood with reference to the following examples. The examples are presented for the purposes of illustration only and are not intended to be construed in a limiting sense.

EXAMPLE 1

270 g of tetraethoxysilane $Si(OC_2H_5)_4$ was hydrolyzed by adding 1300 g of ethanol and 240 g of 0.02N hydrochloric acid and the mixture was stirred for 1 hour. 76 g of glycerin and 81 g of fine silica powder were added to the hydrolyzed mixture and the resulting mixture was stirred for 30 minutes. Next, 36 g of activated carbon and 14 g of carbon black were added to the resulting mixture and the mixture was stirred and ultrasonically dispersed for 1 hour to produce a silica sol with carbon particles dispersed therein. The carbon particle content of the resulting sol was 2.5 wt %. The process was repeated 25 times and viscosity was measured for each. The results are shown in Table 1. It is evident from Table 1 that the variation in viscosity is very small.

TABLE 1

| Carbon Particles (wt %) | Viscosity | | |
| --- | --- | --- | --- |
| | Average | Maximum | Minimum |
| 2.5 | 102 | 106 | 99 |
| 1.0 | 71 | 73 | 70 |
| 2.0 | 93 | 95 | 92 |
| 3.0 | 156 | 160 | 153 |
| 4.0 | 308 | 310 | 303 |
| 6.0 unstable | 673 | 859 | 320 |

The carbon particle content was varied between 1 wt % and 6 wt % as the viscosity (cp) was measured. The results are also shown in Table 1. When the carbon particle content was between 1 and 4 wt %, the stability was good.

EXAMPLE 2

Comb electrodes are formed on an alumina substrate by sputtering Cr. Next, Au, NiCr and Au were sputtered, in that order, on the comb electrodes at the portions to which lead wires were connected. That is, the comb electrodes solely of Cr were located at the portions at which a porous silica film with carbon particles dispersed therein was formed and the four-layered electrodes of Cr, Au, NiCr and Au in that order from the substrate were located at the portions of the electrode where lead wires were connected.

The alumina substrate with electrodes thereon was dip coated in the silica sol containing 2.5 wt % of carbon particles, as prepared in example 1, dried at 100° C. for 10 minutes and sintered at 430° C. for 30 minutes, to form a porous silica film with carbon particles dispersed throughout on the alumina substrate and electrodes.

Tetraethoxysilane was hydrolyzed by adding 27.6 g of ethanol of 4 g of 0.02N hydrochloric acid to 46.8 g of tetraethoxysilane and the mixture was stirred for 1 hour. 10 g of fine silica powder was added thereto and the mixture was stirred for 30 minutes to obtain a silica sol. The silica sol was dip coated onto the porous silica film having carbon particles dispersed throughout, dried at 120° C. for 30 minutes and sintered at 400° C. for 20 minutes, to produce a silica film across the upper surface of the porous silica film.

The moisture sensitivity of the humidity sensor is shown in FIG. 11. The linearity of the logarithm of resistance with respect to relative humidity is good. Complicated linearity compensation circuits and a high resistance measuring circuit are not necessary since the resistance is easy to measure even at a low humidity. A temperature compensation circuit is also not required since the temperatures effect on moisture sensitivity is small.

In summary, since the humidity sensor prepared in accordance with the invention includes an insulating substrate, a pair of electrodes formed on the insulating substrate, a porous silica film containing carbon particles formed on the substrate and electrodes, and a silica film formed on the porous silica film, it is possible to vary the conductivity freely by controlling the carbon particle content of the porous silica film. Thus, it is possible to measure humidity accurately at high temperature and high humidity.

In a humidity measuring apparatus as discussed above, it becomes possible to use a small sized relay and other switching elements as the analog switches, to use a structure other than a flip flop for the frequency divider used for switching the humidity sensor, and to use a comparator element as the voltage judging circuit. Because of the direction of the current flow path in the humidity sensor is changed, the characteristics of the humidity sensor are not changed due to electrolysis or the like making it possible to accurately measure humidity over a long time period resulting in a humidity measuring apparatus having high reliability.

The humidity sensor in accordance with the invention has good linear correlation between the change in impedance and the change in relative humidity. The humidity sensor is capable of accurately measuring a wide range of humidity levels with a simple circuit and the resistance is easily measured at low humidity when the resistance is high. It is also possible to produce a humidity sensor which does not require a logarithm amplifier, since there is a linear relationship between relative humidity and resistance. In addition, a temperature compensation circuit is not necessary since the moisture sensitivity dependence on temperature is small. Thus, it is possible to use the simplified humidity measuring circuit and to produce a highly accurate humidity measuring device at a low cost.

Even in a severe environment, if the carbon particle content of the silica sol is less than about 4 wt. %, the carbon particles in the porous silica film do not deteriorate and remain chemically stable, even at high temperature. Furthermore, since the change in the electrical characteristic is small with respect to time, the humidity sensor may be used in a highly accurate humidity control device.

As described above, the humidity sensor in accordance with the invention is highly accurate and reliable. The humidity sensor is applicable to a wide variety of fields which require humidity measurement and humidity control.

It will thus be seen that the objects set forth above, among those made apparent from the preceding description, are efficiently attained and, since certain changes may be made in carrying out the above method and in the construction set forth without departing from the spirit and scope of the invention, it is intended that all matter contained from the above description or shown in the accompanying drawings shall be interpreted as illustrative and not in a limiting sense.

The invention accordingly comprises the features of construction, combination of elements, and arrangement of parts which will exemplified in the construction hereinafter set forth, and the scope of the invention will be indicated in the claims.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A humidity measuring apparatus comprising:
   humidity sensor means for sensing humidity as a function of resistance;
   a reference resistor having a predetermined resistance value;
   a reference capacitor having a predetermined capacitance;
   charge switching means for selectively coupling one of said reference resistor or said humidity sensor means in series to said reference capacitor to charge said reference capacitor;
   voltage judging means for determining whether the terminal voltage of the reference capacitor is at about a predetermined high voltage (H) or at about a predetermined low voltage (L);
   charge/discharge switching means for selectively charging and discharging said reference capacitor in accordance with the output of said voltage judging means producing an oscillating charge/discharge cycle in response to the output of the voltage judging means;
   sensor direction switching means coupled to said charge/discharge switching means for inverting the direction of current flowing through said humidity sensor means during at least a portion of the period said reference capacitor is charged through said humidity sensor means in response to the output of the charge/discharge switching means;
   determining means coupled to said voltage judging means for determining the resistive value of said humidity sensor means and said humidity as a function of the charge/discharge cycle.

2. A humidity measuring apparatus of claim 1, wherein said humidity determining means comprises:
   oscillation frequency counter means for counting the number of charge/discharge cycles of said reference capacitor which are repeated during a predetermined time period;
   humidity sensor resistance value calculating means for calculating a resistance value for said humidity sensor means in accordance with said number of repeated charge/discharge cycles when said reference capacitor is coupled to the reference resistor for charging and said number of repeated charge/discharge cycles when said reference capacitor is coupled to said humidity sensor for charging; and
   humidity identifying means for identifying the humidity from said resistance value of said humidity sensor calculated by said humidity sensor resistance value calculating means.

3. The humidity measuring apparatus of claim 1, wherein the sensor direction switching means inverts the direction of current periodically.

4. The humidity measuring apparatus of claim 3, wherein the sensor direction switching means inverts the direction of current that flows in the humidity sensor means in each direction determined in response to the output of the voltage judging means.

5. The humidity measuring apparatus of claim 1, further comprising a discharge resistor coupled to said charge/discharge switching means, said discharge resistor providing a load resistance for said reference capacitor during the discharge of said reference capacitor.

6. The humidity measuring apparatus of claim 1, wherein said humidity sensor means includes a first terminal and a second terminal, said humidity sensor means and said reference resistor being electrically connected to said charge switching means for alternative connection to the reference capacitor, said sensor direction switching means further comprising a first switch connected to said first terminal of said humidity sensor means and a second switch connected to said second terminal of said humidity sensor means, said sensor direction switching means inverting the direction of current flowing through said humidity sensor by switching the electrical connection of said charge switching means and said humidity sensor means between said first and second terminals of said humidity sensor.

7. The humidity measuring apparatus of claim 6, wherein said sensor direction switching means further includes flip flop means clocked by the output of said voltage judging means, said first and second switches being actuated by an output from said flip flop means.

8. The humidity measuring apparatus of claim 7, wherein said voltage judging means comprises a logic inverting gate having hysteresis properties.

9. The humidity measuring apparatus of claim 1, wherein said charge/discharging switching means, said sensor direction switching means and said charge switching means include analog switches.

10. The humidity measuring apparatus of claim 1, wherein said humidity sensor includes an insulating substrate; a pair of electrodes formed on said insulating substrate; a porous silica film including carbon particles formed on an exposed surface of said insulating substrate and electrode; and a silica film formed on said porous silica film.

11. The humidity measuring apparatus of claim 10, wherein said electrodes are Cr and include a terminal portion for connection to a lead electrode, said terminal portion further including a layer of Au formed on each Cr electrode, a layer of NiCr formed on the layer of Au and a layer of Au formed on the layer of NiCr.

12. The humidity measuring apparatus of claim 10, wherein a silica sol used in forming said porous silica film contains between about 1 and 4 weight % of said carbon particles.

13. The humidity measuring apparatus of claim 12, wherein said porous silica film contains about 2.5 weight % of said carbon particles.

14. The humidity measuring apparatus of claim 12, wherein the amount of carbon particles is selected to provide a stable humidity sensor.

15. The humidity measuring apparatus of claim 12, wherein the amount of carbon particles is selected to provide accurate humidity measurements.

16. The humidity apparatus of claim 12, wherein said silica sol containing carbon particles is formed by dispersing silica particles and carbon particles in a hydrolyzed solution of silicon alkoxide.

17. The humidity measuring apparatus of claim 10, wherein the insulating substrate is alumina.

18. The humidity measuring apparatus of claim 10, wherein said porous silica film containing carbon particles is produced by forming a silica sol including carbon particles into a film and heat treating said film.

19. The humidity measuring apparatus of claim 10, wherein the electrodes are interleaved comb electrodes.

20. A method of avoiding electrolysis in a humidity or temperature sensor comprising the step of alternatively charging and discharging a capacitor through a moisture sensitive humidity or temperature sensor and through a reference resistor, and periodically changing the direction of charging current through the humidity or temperature sensor in accordance with the charge/discharge cycle of the charging and discharging of said capacitor.

* * * * *